(12) United States Patent
Trail et al.

(10) Patent No.: US 8,377,142 B2
(45) Date of Patent: Feb. 19, 2013

(54) PROSTHESIS

(75) Inventors: Ian Alexander Trail, Manchester (GB); Roderick John Mathias, Leatherhead (GB)

(73) Assignee: Finsbury (Development) Limited, Leatherhead, Surrey (GB)

(*) Notice: Subject to any disclaimer, the term of this patent is extended or adjusted under 35 U.S.C. 154(b) by 0 days.

(21) Appl. No.: 11/765,556

(22) Filed: Jun. 20, 2007

(65) Prior Publication Data

US 2008/0154385 A1 Jun. 26, 2008

(30) Foreign Application Priority Data

Jun. 20, 2006 (GB) .................................. 0612191.7

(51) Int. Cl.
A61F 2/32 (2006.01)
A61F 2/30 (2006.01)

(52) U.S. Cl. ................ 623/21.17; 623/21.15; 623/18.11

(58) Field of Classification Search .... 623/21.15–21.17, 623/18.11, 22.11–23.29; A61F 2/30, 2/32
See application file for complete search history.

(56) References Cited

U.S. PATENT DOCUMENTS

| | | | |
|---|---|---|---|
| 4,231,121 A | | 11/1980 | Lewis |
| 4,242,758 A | * | 1/1981 | Amis et al. ................ 623/20.11 |
| 5,405,400 A | * | 4/1995 | Linscheid et al. ......... 623/21.15 |
| 5,405,401 A | * | 4/1995 | Lippincott et al. ......... 623/21.15 |
| 5,425,777 A | * | 6/1995 | Sarkisian et al. .......... 623/21.15 |
| 5,728,163 A | * | 3/1998 | Maksene .................... 623/21.15 |
| 6,811,568 B2 | * | 11/2004 | Minamikawa ............. 623/21.15 |
| 2006/0052878 A1 | * | 3/2006 | Schmieding ................. 623/23.4 |

FOREIGN PATENT DOCUMENTS

| | | |
|---|---|---|
| EP | 338715 A1 | 10/1989 |
| GB | 1192960 | 5/1970 |
| WO | 92/00709 | 1/1992 |
| WO | 96/25129 | 8/1996 |
| WO | 98/19637 | 5/1998 |
| WO | 03002038 A1 | 1/2003 |
| WO | 2004000174 A1 | 12/2003 |

OTHER PUBLICATIONS

European Search Report for Application No. EP 07 11 0603 dated Sep. 7, 2007, 7 pages.

* cited by examiner

Primary Examiner — Thomas J Sweet
Assistant Examiner — Jason-Dennis Stewart
(74) Attorney, Agent, or Firm — Senniger Powers LLP

(57) ABSTRACT

A distal component for an interphalangeal prosthesis suitable for insertion into a proximal end of a distal phalangeal bone includes a stem portion shaped to be received within a surgically prepared bore in the proximal end of the distal bone. A head portion has an under-surface and an upper-surface, the under-surface of which in use will bear on the bone into which the stem is implanted.

7 Claims, 5 Drawing Sheets

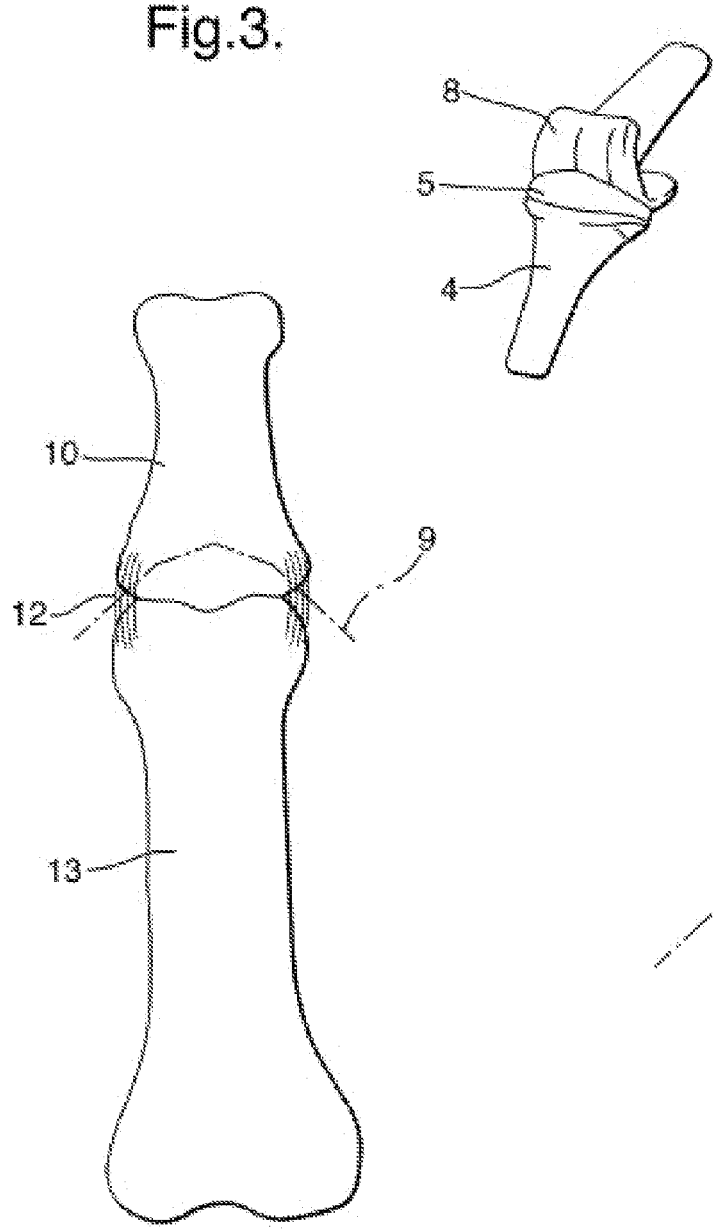
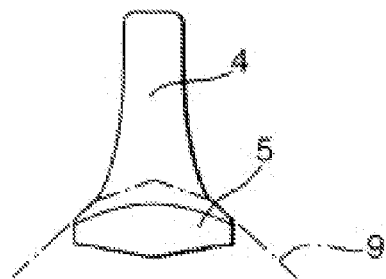

ies.ll
PROSTHESIS

FIELD OF THE INVENTION

The present invention relates to a prosthesis. More particularly it relates to a prosthesis for use in replacing the interphalangeal joint or the metacarpal-phalageal joint. For ease of reference the prosthesis of the present invention will be referred to as an "interphalangeal prosthesis" but it will be understood that the term will cover both prostheses for interphalangeal joints and those for the metacarpal-phalangeal joints whether in the hands or feet.

BACKGROUND OF THE INVENTION

The efficient functioning of the finger and/or toe joints is important to the well being and mobility of the human body. An interphalangeal joint is comprised by the distal end portion of a first phalange and the proximal end portion of the adjacent phalange. Similarly, the metacarpal-phalangeal joint is formed by the distal end of the metacarpus and the proximal end of the proximal phalange. In a normal healthy body these joints will be covered with articular cartilage. The presence of this cartilage allows the bones of the joint to move smoothly and freely through their range of motion.

Diseases such as rheumatoid- and osteo-arthritis can cause erosion of the articular cartilage so that the components of the joint rub together causing pain and further erosion. Bone erosion may cause the bones themselves to attempt to compensate for the erosion which may result in the bone being reshaped. This misshapen joint may cause pain and may eventually cease to function altogether.

Operations to replace the interphalangeal joint are known. In these operations prosthetic joints may be introduced. One type of known prosthesis is a one-piece prosthesis comprising a central body and two oppositely projecting stem portions of reduced cross-section. These stem portions are implanted into the machined ends of bones adjacent the joint. One example of a prosthesis of this kind is described in GB1192960. A modification of these types of prostheses having a hinge-type mechanism between the two stem portions is described in WO96/25129. Whilst joints of this kind go some way to addressing the requirement for an acceptable interphalangeal prosthesis, they suffer from various disadvantages including the long-term stiffening of the joint. It is therefore desirable to provide a prosthesis which more accurately reflects the natural joint.

The natural joint comprises a ball shaped articular head on the distal end of the proximal bone which articulates against a generally socket-shaped surface on the head of the proximal end of the distal bone. Thus, a prosthesis which more accurately reflects the natural joint will generally comprise two separate components such that the resultant movement of the joint most accurately replicates the natural movement of the digit into which it is implanted. Examples of two-part prosthesis comprising one part having an articulating head and a second part having a socket shaped surface on which the head of the first part can articulate are described in WO98/19637, WO92/00709, U.S. Pat. No. 4,231,121 and EP0338715. In each of these prosthesis arrangements there is described a proximal component comprising a shaft for implantation in the resected proximal bone and a head which is at least in part convex and a distal component comprising a shaft for implantation in the resected distal bone and a head which is at least in part concave such that in use the convex head of the proximal component is in articulating contact with the complementary concave head of the distal component.

Whilst these arrangements go some way to resolving the problems detailed above, they still suffer from certain disadvantages and drawbacks. In particular, they generally require substantial resection of the bone into which the prosthesis component is to be inserted before the prosthesis can be used. This is not generally desirable. Further, as the resection required to accommodate these devices is flat to accommodate the flat underside of the prosthesis, there is a high risk of damage to, or a loss of, the collateral ligaments.

FIG. 1 illustrates a schematic plan view of a distal component of a conventional two-part prosthesis which can be inserted into a suitably machined proximal end of a distal bone forming the joint. The distal component of the prosthesis comprises a shaft 1 and a head 2 having a flat bearing component which may be integral with the shaft or may be a separate component which may be removably attachable to the shaft. X represents the minimum amount of material under the articulating surface.

It is therefore desirable to provide a component which provides which reduces the amount of bone which has to be resected to enable the prosthesis to be inserted. However, it will be understood that there should be a depth of material under the articulating surface to provide sufficient support. Preferably it is desirable to provide a prosthesis which when inserted in position enables the collateral ligaments to be retained.

SUMMARY OF THE INVENTION

The present invention relates in one aspect to a distal component for an interphalangeal prosthesis suitable for insertion into a proximal end of a distal phalangeal bone, which component generally comprising:

a stem portion shaped to be received within a surgically prepared bore in the proximal end of the distal bone, said stem portion generally tapering inwardly from a proximal end to a distal end and having a central longitudinal axis extending from the distal end to the proximal end; and a head portion having an under-surface and an upper-surface, the under-surface of which in use will bear on the bone into which the stem is implanted, said head portion extending from the stem portion and being ramped away therefrom at an angle of greater than 90° to the longitudinal axis of the shaft; said upper-surface comprising an articulating surface shaped to enable a cooperating surface on a distal end of a proximal bone forming said joint to articulate there-against.

Other objects and features of the present invention will be in part apparent and in part pointed out hereinafter.

BRIEF DESCRIPTION OF THE DRAWINGS

The present invention will now be described, by way of example, with reference to the following drawings:

FIG. 3 illustrates the component of the prosthesis of the present invention as it interacts with the articulating surface in a cooperating prosthesis which in use will be located in the distal end of the proximal bone;

FIG. 6 is a schematic view from the side of the prosthetic component of the present invention from the side together with a schematic drawing of the joint into which the prosthetic component will be used illustrating the position of the prosthesis and the retention of the ligaments;

DETAILED DESCRIPTION OF THE INVENTION

Figure 1:
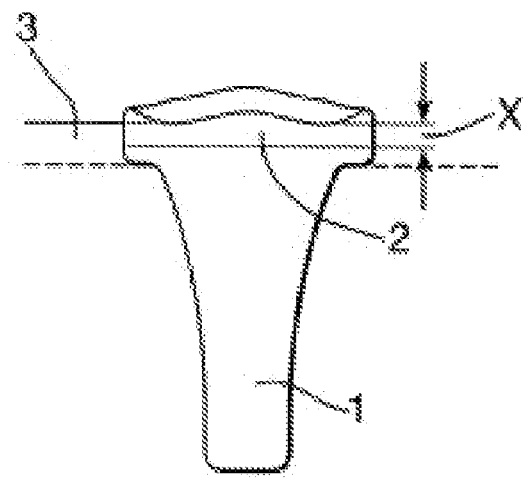
FIG. 1 is a representation of the component of the prosthesis of the prior art.
Figure 2:
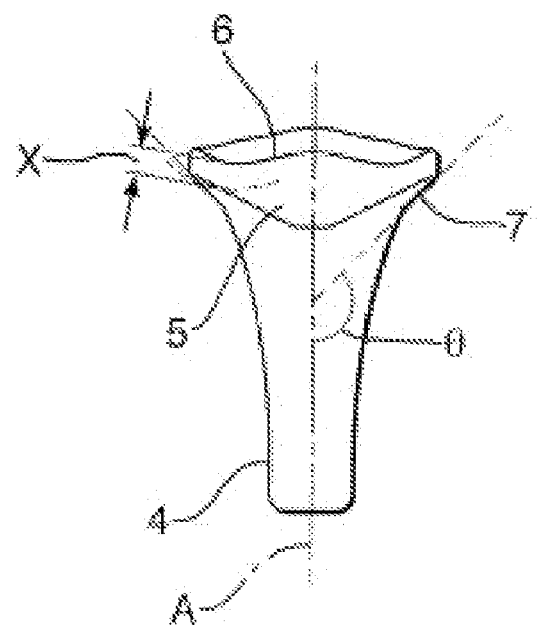
FIG. 2 is a schematic representation of the component of the prosthesis of the present invention.

As illustrated in FIG. 2 the prosthetic component of the present invention comprises a stem portion 4 and a head portion 5. The head portion 5 has an upper surface 6 which in use provides an articulating surface. The undersurface 7 will, in use, bear on the bone into which the stem is implanted. The head component 6 extending from the stem portion 4 and is ramped away therefrom at an angle θ which is greater than 90° to the longitudinal axis A of the shaft. As in FIG. 1, X represents the minimum amount of material required under the articulating surface. It will be noted by comparison with the arrangement illustrated in FIG. 1 that a significant amount of bone may be retained in using the present invention having the generally conical profile.

In the preferred arrangement, the head portion is formed of biocompatible plastics material such as ultra high molecular weight polyethylene and the stem portion from a biocompatible metal such as cobalt chrome.

In use the upper surface 6 of the head portion 5 provides an articulating surface. FIG. 3 illustrates the articulation of the prosthetic component 8 which may be used in the distal end of the proximal bone forming the joint. Generally both ends of bone forming the joint will require resecting and the insertion of a prosthetic component. However, it will be understood that where the distal end of the proximal bone is healthy and does not require the insertion of a prosthesis, the articulating surface 6 of the prosthetic component of the present invention will in use articulate against natural bone.

Figure 4:
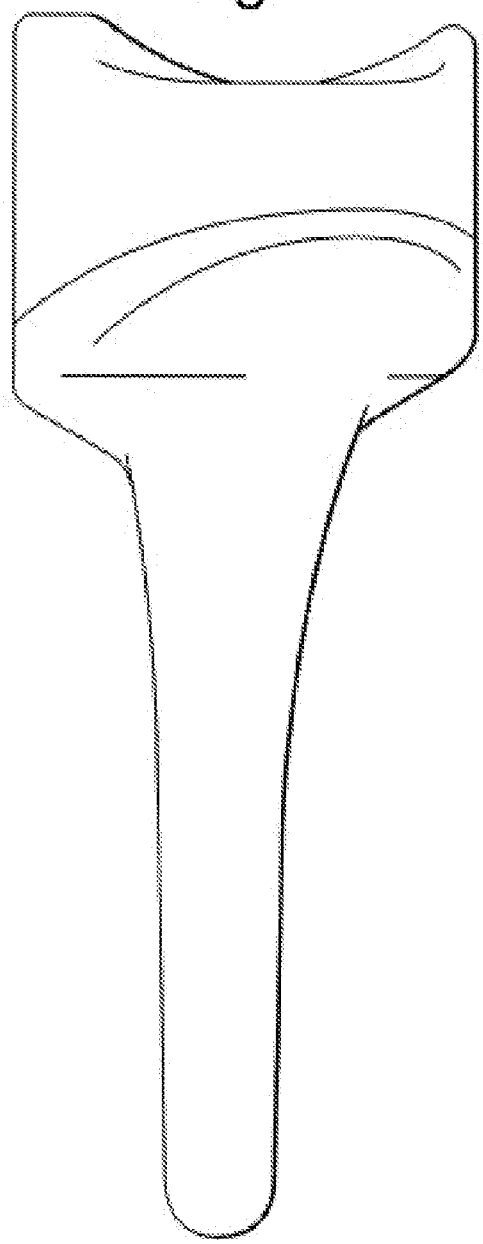
FIG. 4 is a medial/lateral view of the component of the prosthesis of the present invention.
Figure 5:
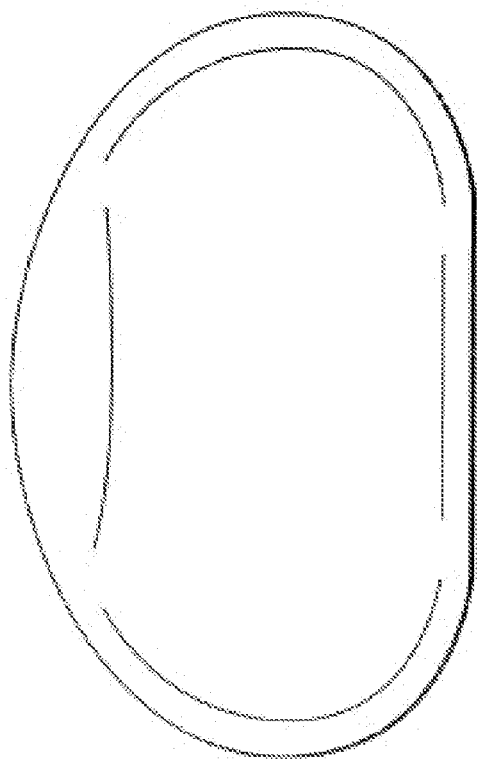
FIG. 5 is a view of the distal end of the device of FIG. 4 with the palmer side to the right.

As illustrated in FIGS. 4 and 5 the overall configuration of the component when viewed from above can be regarded as being generally D-shaped.

The profile of the prosthetic component of the present invention is illustrated by line 9 on the component of FIG. 6. The profile is illustrated by line 9 on the joint illustrated in FIG. 6. This shows the function of the profile of the proximal resection of the middle phalanx 10 in retention of the collateral ligaments 12. It can readily be seen that the conical form of the profile maximizes material thickness in the middle phalangeal component whilst sparing the ligaments. This retention of the ligaments will assist in the correct articulation and functioning of the joint on the distal end of the proximal phalanx 13.

Figure 7:
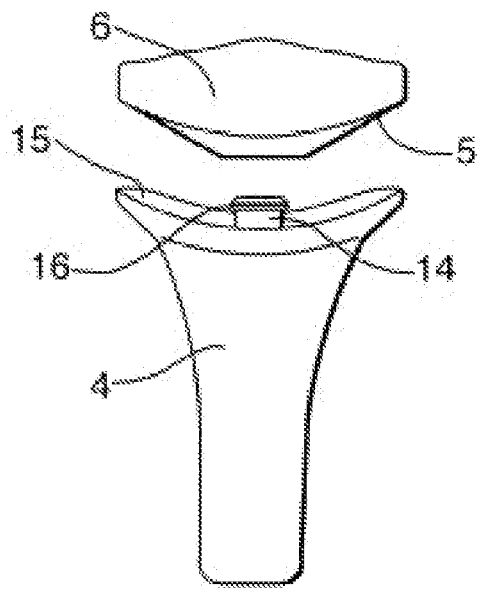
FIG. 7 is a schematic view from the side showing the arrangement in which the head and stem components are separate.
Figure 8:
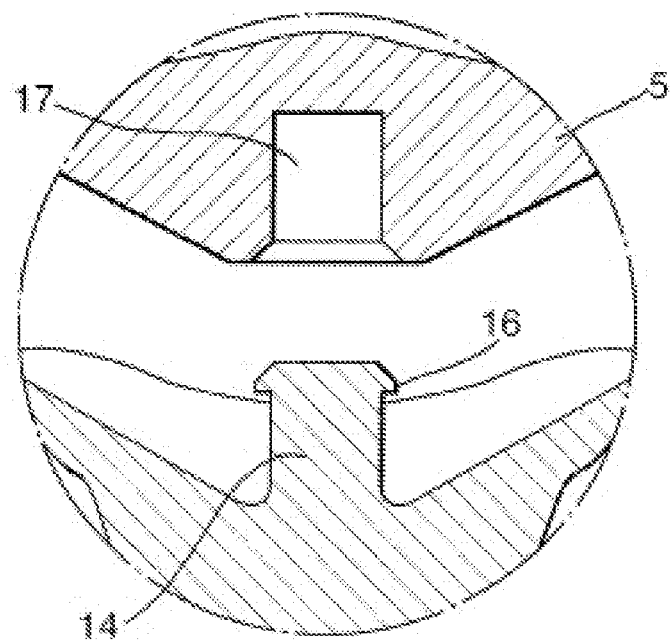
FIG. 8 is an exploded view of the interlocking arrangement between the stalk extending from the stem portion and the bore in the underside of the head portion.

The head portion 5 includes an upper section and a separate lower section. The upper section of the head portion 5 and the stem portion 4 are preferably provided as two components as illustrated in FIG. 7. Here the stem portion includes a stalk 14 extending from and surrounded by the head supporting surface 15 forming at least a part of the lower section of the head that is integrally formed with the stem. The stalk includes a barb 16 extending around its circumference. As illustrated in FIG. 8, the stalk is inserted into a bore 17 provided in the underside of the upper section of the head portion. The upper section of the head portion 5 is preferably a snap-fit onto the stalk 14.

Figure 9:
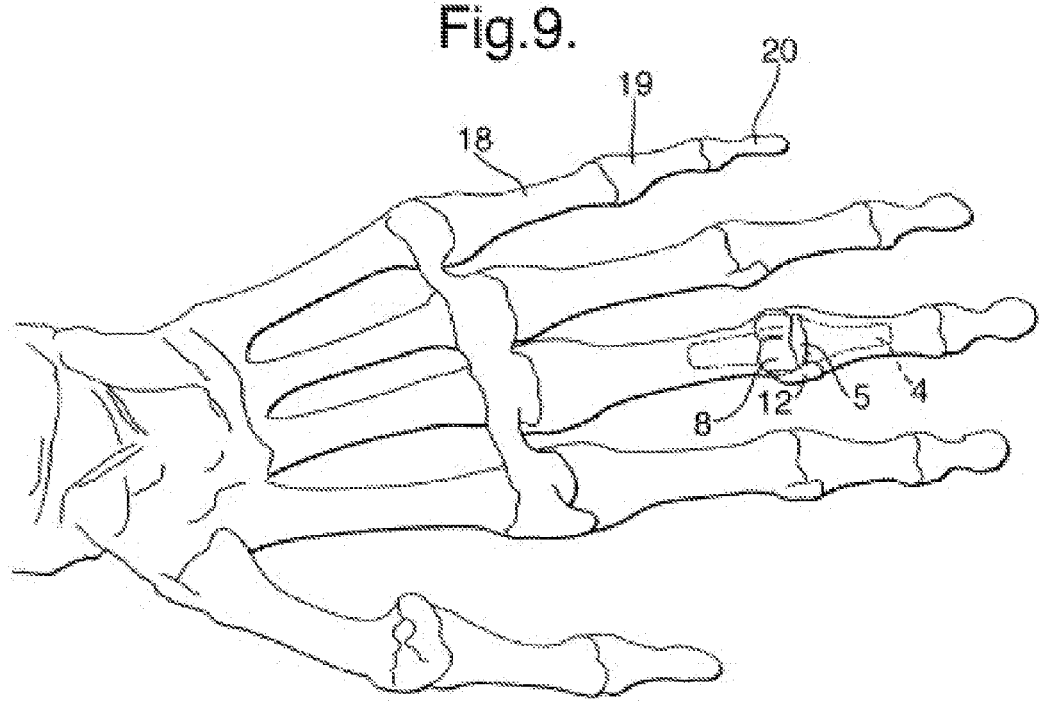
FIG. 9 is a schematic view of the bones of the hand showing the proximal interphalangeal joints between the proximal and middle phalanges; the component of the present invention is shown as part of the prosthesis on the joint of the middle finger.
Figure 10:
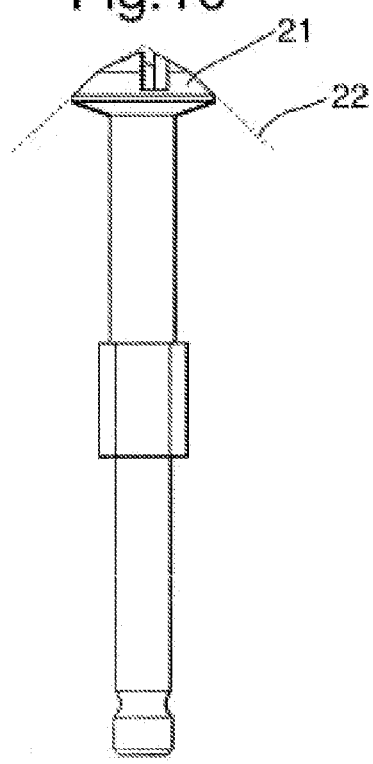
FIG. 10 illustrates a conical mill suitable for the proximal resection of the phalanx into which the prosthetic component of the present invention will be inserted.

The prosthetic component of the present invention located in the interphalangeal joint between the proximal phalanx 18 and the middle phalanx 19 of the middle finger is illustrated in FIG. 9. The finger also includes a distal phalanx 20. The articulating surface of the prosthesis is acting against the articulating surface of a proximal phalangeal component 8.

In order to obtain the conical bore in the proximal end of the bone a conical mill 21 such as that illustrated in FIG. 9 may be used. The conical profile achieved by the mill 21 is illustrated by line 22.

With the arrangement in the present invention, a depth of material is provided to give support for the articulation surface whilst minimizing the amount of bone which has to be resected to enable the prosthesis to be inserted.

As indicated, the special shaping of the component of the present invention minimizes the amount of natural bone which has to be resected. It is generally desirable to maintain as much of the natural bone as possible. However, there is a particular advantage in retaining natural bone in the areas where the ligaments attach. The conical shape of the stem portion of the prosthesis means that a conical resection can be used which will generally allow the connection point for collateral ligaments to be retained. For example, where the prosthesis is for use at the proximal end of the middle phalanx, the resection required to enable the prosthesis of the present invention to be inserted, enables the collateral ligaments which are attached close to the proximal end of the middle phalanx to be retained. Thus it will be understood that a benefit of the present arrangement is that the attachment points of the collateral ligaments can be maintained and there is no risk of the prosthesis interfering with the action of the flexor tendons and the collateral ligaments.

The stem portion and the head portion may be formed as a single piece. In this arrangement, each size of component may be supplied in a number of forms, each matching the range of proximal components with which in size they may be combined. In a preferred arrangement, they may be formed in separate pieces.

In an alternative preferred embodiment, the stem portion and at least a lower section of the head portion may be formed as a single piece such that the stem portion and the section of the head portion which forms the under-surface which in use will bear on the bone into which the stem is implanted is a single piece. Thus this arrangement provides a single element which provides a tray that in use supports a separate upper section of the head portion which provides the upper-surface which in use is the cooperating surface on the distal end of the proximal bone.

In the embodiment in which separate components are used, the components may be interconnected by any suitable means. In one arrangement, a stalk may extend from a supporting cone congruent with said stem portion. In view of the shaping of the stem portion discussed in detail below, when the stalk is present, it will form a perfoliate arrangement. Where the stalk is present, a bore may be provided in the underside of the head portion into which the stalk may be inserted to lock the head portion in position. In a particularly preferred arrangement, the head portion may be a snap-fit on the stalk portion which may include a barb to assist in interlocking the stalk portion in the bore. The barb may extend around the outer circumference of a portion or the whole of the stalk or may simply be one or more flanges extending from the stalk.

This arrangement of the present invention offers a further advantage in that it provides some initial flexibility in the rotational position of the head portion. This flexibility in use enables the surgeon to correct any misalignment in the location of the stem portion of the component in the machined bone.

A further advantage of having separate components is that the prosthesis can be regarded as modular such that the surgeon can select the appropriate stem and appropriate articulating surface for a particular patient. In particular, this modularity allows the surgeon to select independently the most appropriate sized stem, based upon the individual bones which maintaining optimal conformity of bearing surfaces.

Thus it will be understood that in the arrangement in which the upper-surface component is a snap-fit on a stalk, the various possible combinations of implant sizes is matched by a range of snap-on components from which in use the surgeon can select the appropriate ones. From the foregoing, it will be understood that the prosthesis component of the present invention can be provided in any suitable size. Generally, the overall size can be provided in the same five sizes conventionally used, namely the nominal sizes 7, 8, 9, 10 and 11. It will be understood that these sizes describe the maximum width across the upper-surface of the head which is in the dorsal/palmer plane.

The prosthesis of the present invention may be formed of any suitable material. Where the stem portion and the head portion are formed of separate pieces, they may be formed of the same or different materials. In one arrangement, the head portion may be formed from a biocompatible plastics material. Suitable biocompatible plastics materials include ultra high molecular weight polyethylene. In the same or a different arrangement, the stem portion may be formed from a biocompatible metal or polymeric material. Suitable biocompatible metal materials include cobalt-chrome, titanium, titanium alloys, titanium coated cobalt-chrome, and stainless steel.

The surface of the stem portion may have a polished surface. Alternatively, the stem portion may have a roughened surface. In one arrangement, the stem may be ribbed.

The articulation surface of the head portion may be of any suitable shape but is preferably shaped to mimic that of the natural bone. In one arrangement, it will be shaped to accept the bicondular features on the distal end of the proximal bone. However, concave configurations may also be used.

The stem portion is preferably elliptical in cross-section. Where the head portion of the prosthesis is separate from the stem component, the upper surface of the stem component preferably provides a tray on which in use the head portion sits. The tray is preferably higher on one side than on the other. The higher side is preferably the palmer side. Thus the tray can be envisaged as being of a ruff configuration around the stalk, where present. In one embodiment the outer profile of the tray can be considered as being generally D-shaped (albeit with some curvature on both sides) with the most curved side being located in use on the dorsal side of the joint.

The notional line from the end of the stem to the edge of the upper-surface may be of any suitable configuration. It may be a linear slope or it may be curved either in a convex or a concave manner.

The component of the present invention may be provided in a kit additionally including a proximal component for an interphalangeal prosthesis suitable for insertion into a distal end of the proximal phalangeal bone.

What is claimed is:

1. A distal component for an interphalangeal prosthesis suitable for insertion into a proximal end of a distal phalangeal bone, said component comprising:
   a stem portion shaped to be received within a surgically prepared bore in the proximal end of the distal phalangeal bone, said stem portion generally tapering inwardly from a proximal to a distal end and having a central longitudinal axis extending from the distal end to the proximal end, said stem portion additionally comprising a head supporting surface formed as a single piece with said stem portion, the underside of said head supporting surface bearing on the distal phalangeal bone into which the stem is implanted and extending from the stem portion and being ramped away therefrom at an angle of greater than 90° to the longitudinal axis of the shaft; and
   a head portion having an under-surface and an upper-surface, the under-surface of which in use will face the distal phalangeal bone into which the stem is implanted, said head portion extending from the stem portion and being ramped away therefrom at an angle of greater than 90° to the longitudinal axis of the shaft; said upper-surface comprising an articulating surface shaped to enable a cooperating surface on a distal end of a proximal phalangeal bone to articulate there-against as a hinge joint, the head portion having a bore therein;
   wherein the stem portion in use supports a separate upper section of the head portion, wherein the stem portion includes a stalk extending from and surrounded by the head supporting surface and including a barb to assist in interlocking in the bore, the bore and barb of the stalk being constructed for snap-fit, locking interengagement upon reception of the stalk and barb in the bore to connect the head portion and the stem portion.

2. A distal component for an interphalangeal prosthesis according to claim 1 wherein the barb extends around the outer circumference of the stalk.

3. A distal component for an interphalangeal prosthesis according to claim 1 wherein an upper section of the head portion is formed from a biocompatible plastics material.

4. A distal component for an interphalangeal prosthesis according to claim 3 wherein said biocompatible plastics materials is ultra high molecular weight polyethylene.

5. A distal component for an interphalangeal prosthesis according to claim 1 wherein the stem portion is formed from a biocompatible metal or plastics material.

6. A distal component for an interphalangeal prosthesis according to claim 5 wherein said biocompatible metal material is cobalt-chrome, titanium, titanium alloys, titanium coated cobalt-chrome, or stainless steel.

7. A distal component for an interphalangeal prosthesis according to claim 1 where the articulating surface is shaped to accept bicondular features of the distal end of the proximal phalangeal bone to form the hinge joint.

* * * * *